(12) United States Patent
Barie et al.

(10) Patent No.: US 6,945,089 B2
(45) Date of Patent: Sep. 20, 2005

(54) MASS-SENSITIVE SENSOR

(75) Inventors: Nicole Barie, Stutensee (DE); Ulrich Stahl, Karlsruhe (DE); Michael Rapp, Eppelheim (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 25 days.

(21) Appl. No.: 10/117,067

(22) Filed: Apr. 1, 2002

(65) Prior Publication Data

US 2005/0011251 A1 Jan. 20, 2005

Related U.S. Application Data

(63) Continuation-in-part of application No. PCT/EP00/09424, filed on Sep. 27, 2000.

(30) Foreign Application Priority Data

Oct. 15, 1999 (DE) .......................................... 199 49 739

(51) Int. Cl.[7] .......................... G01N 27/00; G01N 33/00
(52) U.S. Cl. .................... 73/24.06; 73/30.04; 73/31.05; 73/31.06; 73/54.41; 73/61.45; 73/61.75; 73/61.79; 73/579; 310/313 R
(58) Field of Search ................... 73/24.01, 24.03–24.06, 73/30.01, 30.04, 31.01, 31.02, 31.03, 31.05, 31.06, 32 A, 32 R, 53.01, 54.01, 54.02, 54.23, 54.41, 61.45, 61.75, 61.79, 579; 310/360, 316, 313 R, 313 B, 320

(56) References Cited

U.S. PATENT DOCUMENTS

| | | | | |
|---|---|---|---|---|
| 5,283,037 A | * | 2/1994 | Baer et al. ............... | 422/82.01 |
| 5,306,644 A | * | 4/1994 | Myerholtz et al. .......... | 436/149 |
| 5,536,317 A | * | 7/1996 | Crain et al. ................. | 118/664 |
| 5,556,473 A | * | 9/1996 | Olson et al. ................ | 118/719 |
| 5,709,753 A | * | 1/1998 | Olson et al. ................ | 118/719 |

FOREIGN PATENT DOCUMENTS

EP    632266 A2   *  1/1995   .......... G01N/29/02

OTHER PUBLICATIONS

"Parylene Properties & Characteristics", Printed Nov. 22, 2004, http://www.vp-scientific.com/parylene_properties.htm, pp. 1–4.*

"Parylene General Properties/Benefits", 1998, Advanced Coating, http://advancedcoating.com/gen.html, p. 1.*

"Description of Parylene", 1998, Advanced Coating, http://advancedcoating.com/tech1.html, pp. 1–2.*

"Physical and Mechanical Properties", 1998, Advanced Coating, http://www.advancedcoating.com/phys-mech.html, pp. 1–2.*

"Electrical Properties", 1998, Advanced Coating, http://www.advancedcoating.com/elec.html, pp. 1–2.*

* cited by examiner

Primary Examiner—Hezron Williams
Assistant Examiner—Rose M. Miller
(74) Attorney, Agent, or Firm—Klaus & Bach

(57) ABSTRACT

In a mass-sensitive sensor consisting of an acoustic surface wave component on the basis of shear waves, the sensor includes a substrate with an active surface carrying two different layers, one which is a parylene layer of a thickness of between 0.2 and <1.6 μm, which has been produced on the substrate by a vacuum-based deposition method and is capable of generating Love waves and the second layer forms a utilization layer, which interacts with an analyte disposed in a medium contacting the utilization layer.

8 Claims, 2 Drawing Sheets

MASS-SENSITIVE SENSOR

This is a continuation-in-part application of international application PCT/EP00/09424 filed Sep. 27, 2000 and claiming the priority of German application 199 49 739.7 filed Oct. 15, 1999.

BACKGROUND OF THE INVENTION

The invention relates to a mass-sensitive sensor consisting of an acoustic surface wave (OFW) component on the basis of shear waves.

A way to increase the sensitivity and, consequently, to improve the detection limits of acoustic sensors is to use a special type of waves, the Love-waves.

Love-waves are generally acoustic modes which propagate in a layer structure, which consists of a substrate and a thin wave-conducting layer (homogeneous, or respectively, compact film whose thickness is in the outer of the wavelength) disposed on the substrate.

In order to stimulate Love-waves, the transversal acoustic sound velocity in the deposited layer must be smaller than that in the piezo-electric substrate. Only under this condition, it is possible to transfer a surface skimming bulk wave (SSBW) into a Love-wave. The greater the difference between the two velocities is the more efficient is the conversion of the wave types and, consequently, the greater is the sensitivity gain.

In the case of shear wave components, the surface wave generated on a substrate can be concentrated, by the acoustically softer layer material on the surface (if no periodic mass grids are present) or, respectively, they can be additionally concentrated (if periodic mass grids are present), which results in an increased sensitivity of this wave type to disturbances at the surface and which, in this way, provides for a high mass sensitivity.

Abbreviations which will be used herein:

LW-Component=a component based on Love-waves
SSBW=shear wave (Surface Skimming Bulk Wave)
RW=Rayleigh-waves
OFW/SAW=surface wave

STATE OF THE ART

Love-waves, particularly the mass-sensitivity depency of LW-components on the layer thickness of the wave conducting layer, have been described theoretically by numerous authors and have also been observed in experiments. In this process, various concepts for the realization of LW-sensors have been utilized which are all based on the operation of the component as a delay line. Below a selection of same experimental mark is presented:

Kovacs et al.; "Love waves for (bio)chemical sensing in liquids", Proc. IEEE Ultrasonic Symp. (1992), 281–285 use ST quartz components (operation as delay line) and $SiO_2$ as wave carrying layer.

The components used had, in an uncoated state, a base frequency of 122.5 MHz with an insertion attenuation of about 20 dB.

$SiO_2$ layers were deposited by sputtering up to a thickness of 1.46 µm, wherein however these layer thicknesses were clearly below the calculated optimal thickness for the given system which is about 6 µm.

Thicker layers could not be produced by the authors because of adhesion problems and internal tensions.

The experimental determination of the mass sensitivity occurred by deposition of photo resist films.

Gizeli, E. "Design considerations for the acoustic waveguide biosensor", Smart Mater. Struct. 6 (1997) 700–706 describes mostly experimental considerations concerning components with polymer wave-conducting layers.

The LW-sensors produced are based on OFW components (delay line) with the substrate material quartz (Y-section), a base frequency of 110 MHz and on insertion attenuation of about 29 dB.

As wave conducting layer, preferably poly-methyl-methacrylate (PMMA) was used, which was deposited by a spin coating process up to a thickness of 1.6 µm.

Also in this case the maximum produced layer thickness was less than the theoretically predicted optimal layer thickness of about 3 µm. The limiting factor was in this case the rapid increase of the attenuation of the LW-components with the layer thickness of the wave conducting PMMA layer.

The change of the insertion attenuation and of the resonance frequency of the components was observed experimentally dependent on the layer thickness of the PMMA-film. The examination of the mass sensitivity occurred by a repeated deposition of Langmuir-Blodgett-films and resulted in a 3 (1.0 µm PMMA) or respectively, 7 fold (1.6 µm PMMA) increased sensitivity in comparison with uncoated quartz component.

Wave conducting layers in a layer thickness range, which includes the theoretically calculated optimum, were realized for the first time by Du, Harding et al., "An experimental study of Love wave acoustic sensors operating in liquids", Sens. Act. A60 (1997) 54–61.

They operate with components (delay line), which are based on St-quartz, with a base frequency of 124 MHz and an insertion attenuation of about 23 dB.

As wave conducting layer $SiO_2$ with a layer thickness range of 0 to 7.3 µm was deposited by sputtering.

In order to utilize in biosensor systems commercially available SAW components as mass-sensitive transducers, the SAW surface must be coated with a bio-sensitive layer of proteins which then detect the respective analyte molecules in the sample.

These reactions occur in aqueous media.

However, when used in aqueous media and with the required immobilization procedures, the structures present on the components and the bond wires of aluminum need to be protected since otherwise, they will not withstand the respective chemical conditions.

A coating of the components with quartz does not protect the aluminum structures on the SAW components or it protects them only inadequately.

It is the object of the present invention to provide a mass-sensitive sensor of the type described above wherein the sensitive aluminum structures of the sensor are sufficiently protected against corrosion while the sensitivity is increased.

SUMMARY OF THE INVENTION

In a mass-sensitive sensor consisting of an acoustic surface wave component on the basis of shear waves, the sensor includes a substrate with an active surface carrying two different layers, one which is a parylene layer of a thickness of between 0.2 and <1.6 µm, which has been produced on the substrate by a vacuum-based deposition method and is capable of generating Love waves and the second layer forms a utilization layer, which interacts with an analyte disposed in a medium contacting the utilization layer.

In many cases however a parylene layer with a thickness greater than 1.2 µm is ineffective. The parylene layer is preferably between 0.4 0.8 µm thick.

Parylene is a group designation for thermoplastic polymers with phenyl rests, which are bonded in the 1.4 position by way of ethylene bridges. Below their melting points parylenes are resistant to solvents; they have excellent di-electric properties and they are excellent barrier plastic materials. They are mainly used as intermediate layers for insulators, for the passivation of semiconductors and for a crater-free coating of printed conductor busses.

Parylenes are manufactured by dehydrating dimerization of p-xylol to paracyclophane by way of 1.4-chinodimethane which is formed intermediately and which polymerizes upon condensation from the gas phase on suitable substrates to form thin films of poly (p-xylylene).

Besides poly(p-xylylene) among others, the parylenes poly (2-chloro-p-xylylene)s and poly(dichloro-p-xylylene)s, which are accessible from the corresponding p-xylol derivatives, are suitable for coating.

The polymer parylene-C is applied as a layer with a thickness of 0.2–1.6 $\mu$m as wave conducting layer to form a protective layer for SAW components.

The additional vapor deposition of a polymer layer is small, the components coated with a protective layer have attenuations of −2.5 to −3.0 dB (with a phase zero passage of −10°).

The parylene film is extremely smooth which is very important with the use of SAW components, since the propagation of surface waves is disturbed by irregularities of the surface resulting in additional attenuation losses and a reduced sensitivity.

The protective coating is to protect the SAW component from the corrosive attack by aqueous solutions, acids, bases, and aggressive reagents. Parylene coated components were observed to withstand attacks even after exposure times of several hours and even after heating of the sensor in hydrochloric acid (0.5 M). The parylene film therefore provides for excellent protection of the component from corrosive attacks.

Another advantage of the parylene layer resides in the fact that the active layer adheres better to this layer than to quartz.

A coating with polymethylmethacrylate (PMMA) as wave-conducting layer has the following disadvantages in comparison with parylene:

No vacuum deposition method can be used, that is a spin coating process must be used which does not provide for smooth and parallel planar layers and results in a worse adhesion than can be achieved with surfaces pretreated in a vacuum which can be treated there in situ by gas-chemical or plasma cleaning procedures.

PMMA has a relatively high intrinsic attenuation. In the above-mentioned publication, this was even the limiting factor since the attenuation was in the optimum already at 25 dB. Our optimum is already at an attenuation of 15 dB.

Overall the utilization of parylenes in accordance with the invention as wave conductive layer is attractive because of:

its low sound velocity and consequently, the small thickness of the optimally wave conducting layer, a high protection effect because of its partially crystalline molecular structure already with this layer thickness, freedom of tensions, since the depositing method is vacuum based, cold and therefore low energetic, good planar parallelism, because of the vacuum based deposition method and good adhesion since the vacuum-based deposition method permits an ideal pretreatment of the surfaces.

Below the invention will be described in greater detail on the basis of examples with reference to the figures. In this connection, FIG. 1 shows transmission curves of sensors with parylene layers of different thicknesses and FIG. 2 shows the change of the sensor sensitivity depending on the layer thickness of the parylene film.

Essential differences between the sensor according to the invention and those according to the state of the art are:

1. Different Component
    that is—a different substrate material
        —different insert attenuation
        —different resonance frequency range.

As basis of the LW-construction elements for the first time commercially available components are used. Since these components are produced in large numbers, they can be acquired inexpensively. In contrast to the components described by the above authors, which are produced specifically for the respective application the components used herein are substantially smaller and have an extremely low inherent attenuation and a high resonance frequency. The design of the components used differs significantly from that of the simple delay lines. As substrate material 36° -rot. XY-LiTaO$_3$ is employed.

A resonator structure is utilized which includes, except for the stimulating transducer, passive reflectors, which reflect 50% of the acoustic energy radiated outwardly back into the component. All other authors utilize pure delay lines which, particularly with longer delay distances and higher intrinsic attenuation values of the wave conducting layer, tend to have a high insert attenuation and consequently background static.

For the 36YX. LT STW-component the following values apply:

$F_0$=380 MHz
$\lambda$=10.8 $\mu$m
$v_s$=4160 m/s
$r_s$=7450 kg/m$^3$
$\mu_s$9.4×10$^{10}$ Nm$^2$ 2. Other Wave Conducting Layer (Polymer Coating).

A polymer coating (parylene-C) is used.

In order to utilize commercially available SAW components as mass sensitive transducers in biosensor systems the SAW-surface must be coated with a biosensitive layer of proteins which then detects the respective analyte molecules in the sample.

This reaction occurs in aqueous media.

However, the utilization in these aqueous media and also the necessary immobilizing procedures require a protection of the structures and bond wires of aluminum disposed on the component, since otherwise they will not withstand the respective chemical conditions.

A coating of the components with quartz or respectively, one of the other layers mentioned does not protect the aluminum structures on the SAW component or it protects them only inadequately.

The mass sensitivity of an acoustic component depends on the acoustic energy density at the surface in relation to the total acoustic energy of the OFW. Because of the effect of the wave conducting layer of a component based on Love waves (LW-components) the acoustic energy density at the surface is increased, whereby a high sensitivity can be achieved. The thickness of this applied wave-conducting layer has a strong influence on the mass sensitivity. With increasing thickness of the layer, the sensitivity passes a maximum.

This means that, with a given layer system and a defined wave length, the thickness of the wave conducting layer must be optimized in order to achieve maximal sensitivity.

The high sensitivity of the LW-components is based on a wave conducting effect of the coating. Since Love-waves are surface waves, the largest part of the acoustic energy is disposed in the wave-conducting layer and in the regions near the surface of the substrate. The distribution of this energy and consequently the sensitivity depends, at a given wave length, on the thickness of the coating.

With a small thickness ($h<<\lambda=10.8$ μm) of the wave conducting layer the acoustic field penetrates deep into the piezo electric substrate.

With increasing thickness of the layer, the acoustic energy is increasingly concentrated in the wave-conducting layer and, as a result, at the surface whereby the sensitivity is increased.

When finally almost all of the acoustic energy is concentrated in the surface layer, an increase in the thickness of the layer results in a reduction of the sensitivity since the energy is distributed over the full thickness of the layer so that the energy density of the wave drops.

Consequently, there is an optimal layer thickness at which for a particular wave-length a maximum sensitivity is obtained.

With thick layers furthermore more than one Love-wave can be stimulated, wherein however the mode of zero order is more sensitive than the modes of higher order, since then the spatial distribution of the acoustic energy has the greatest concentration at the surface.

Generally, the insert attenuation of LW components first decreases with increasing thickness of the wave-conducting layer, reaches a minimum and then increases with further increasing layer thickness. For this behavior, two opposing effects are responsible. On one hand, the acoustic energy is guided in the wave-conducting layer by the conversion of SSBW to the Love-wave instead of being radiated into the substrate, which results in a lowering of the insert attenuation.

On the other hand, the application of the wave-conducting layer as such provides for an additional attenuation.

Altogether, the result is that, with lower layer thicknesses, first the attenuation of the component drops, since the attenuation resulting from the thin coating is still negligible. Only with increased layer thicknesses, the attenuation in the wave conducting layers becomes more noticeable so that the insertion attenuation of the component increases again.

EXPLANATION OF THE INVENTION BASED ON FIG. 1

The attenuations of the LW components are greater than those of the uncoated components and increase slightly with increasing layer thickness.

This behavior is contrary to the theoretically predicted behavior and contradictory to the experimental curves as determined by other authors as described earlier. The reason here for is mainly the special design of the components used: On one hand, the components are operated as resonators and not as delay lines as they are in the experiments described earlier. Therefore the approximations of theoretical deductions, which generally relate to delay lines, cannot be used.

On the other hand, the components employed are so-called "low-loss-filters" which means that the insert attenuation of the uncoated components in air is, with about 1.4 dB, very low already from the start. Therefore, with the wave guided along the surface, the effect of the attenuation reduction can not be as drastic as it is possible with the components of the other authors. Rather, the contribution of the wave-conducting layer to the attenuation becomes effective relatively fast.

The insertion attenuation of 18 dB critical for the operation of the components in the high-frequency oscillator electronics is achieved only with parylene layer thicknesses of about 3.5 μm.

2. Parylene as Wave Conducting Layer in Liquids.

The dependency of the mass sensitivity of the LW components on the deposited wave-conducting layer was determined experimentally by the deposition of BSA on the surface. In this way, the optimal layer thickness for maximal sensitivity could be determined.

For the examination of the mass sensitivity of the LW-components as dependent on the parylene layer thickness BSA solutions in a concentration of 2 mg/ml were used so as to operate in the determined saturation range of the adsorption and to obtain thereby maximum sensor signals. The frequency changes achieved thereby are shown in FIG. 2 depending on the layer thickness of the wave conducting layer of about 2 $ng/mm^2$.

The frequency changes of the components upon separation of BSA depends on the thickness of the wave conducting layer.

Figure 1:
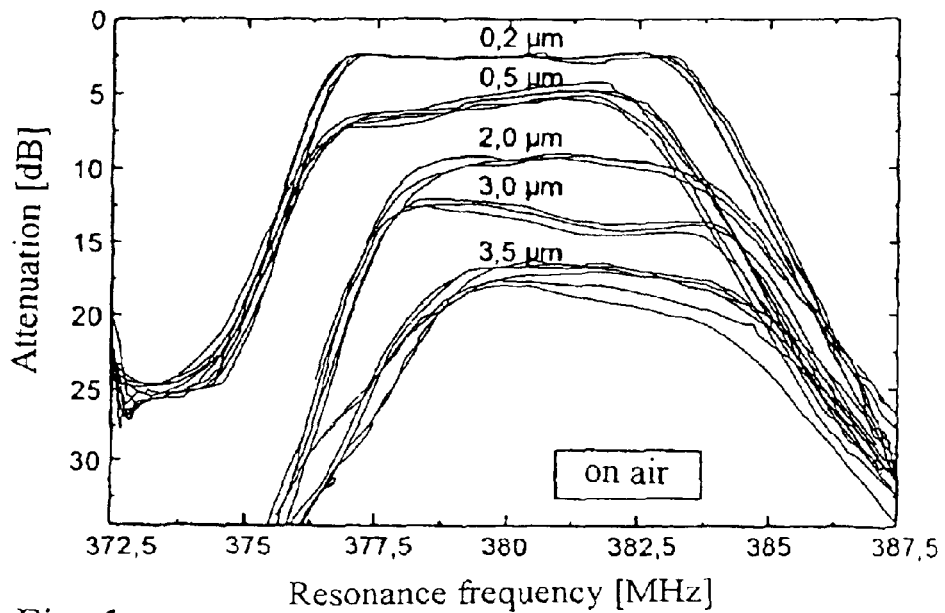
FIGS. 1 and 2 show the transmission curves in air of acoustic components with parylene layers of different thicknesses.
Figure 2:
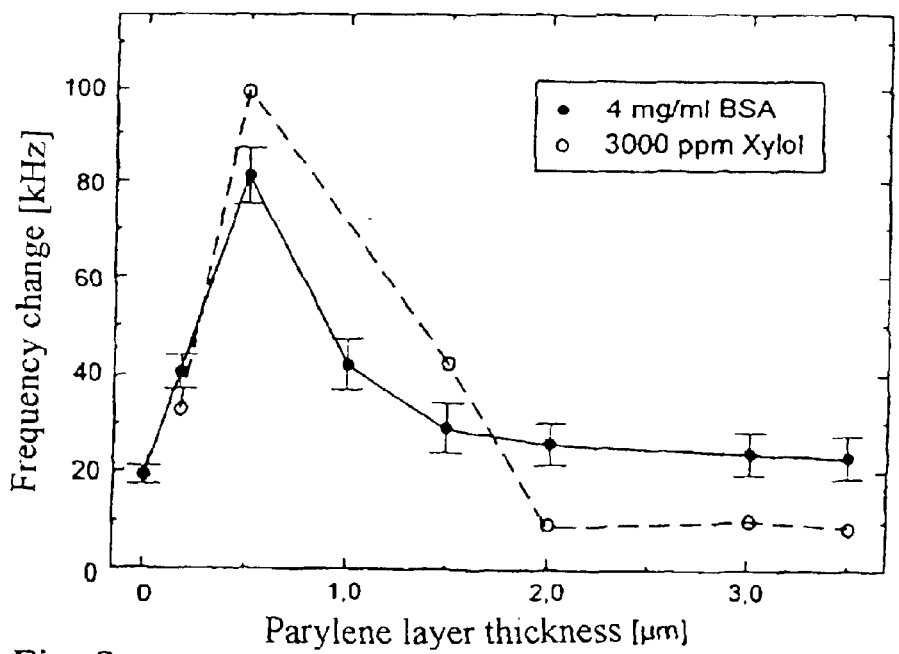
Figure 3:
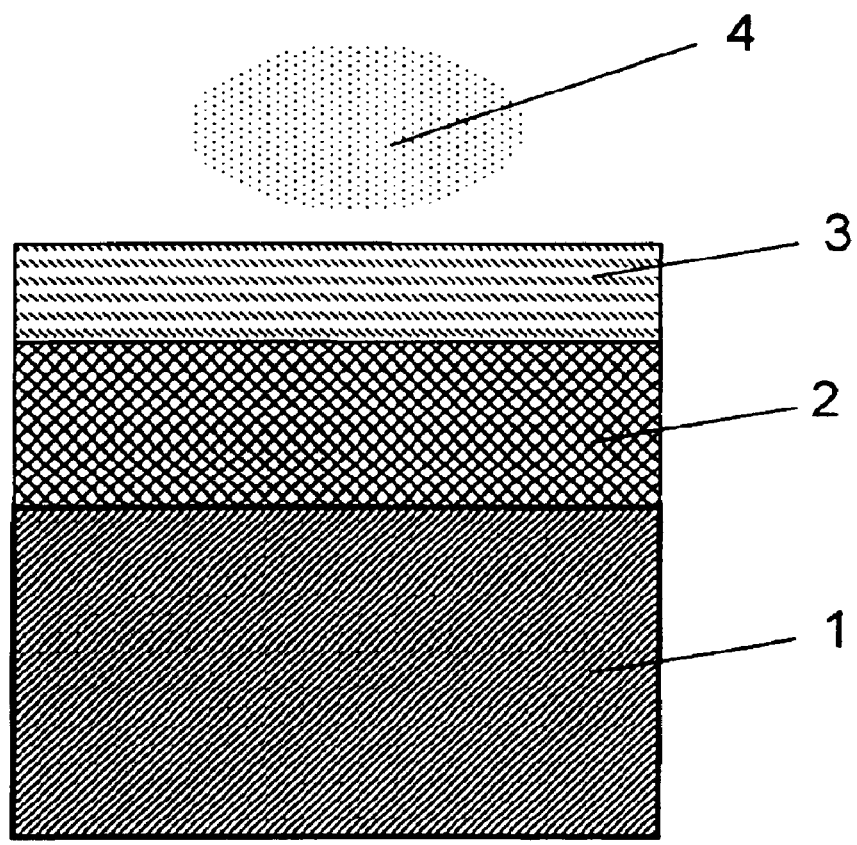
FIG. 3 shows in cross-section a sensor structure including a parylene layer.

As shown in FIG. 2, the frequency change resulting therefrom increases with increasing parylene layer thickness to a maximum at 0.5 μm. The frequency change of 82 kHz reached at this maximum is greater by a factor of 4.3 than that of an uncoated component (without parylene layer, but with a reaction layer). Taking into consideration triple the background noise, the detection limit achieved in 20 mM phosphate buffer is 2.9 $pg/mm^2$. (In comparison herewith, for uncoated STW components under the same condition, a detection limit of 13.3 $pg/mm^2$ can be determined.)

For the determination of the detection limit, the resonance frequency of the LW-components in air or respectively, by application of a distilled water sample and 20 mM phosphate buffer was observed for 10 mm. The frequency noise in air was about 4 Hz, in water about 20 Hz and in 20 mM phosphate buffer about 40 Hz; the different parylene thicknesses had almost no influence.

The determined detection limits of the LW sensors presented herein are low enough to detect surface charges which are clearly below those of typical protein monolayers, which have generally a surface coverage of several $ng/mm^2$ (for example, 2 $ng/mm^2$ for BS, 4 $ng/mm^2$ for IgG antibodies).

The described parylene coated SAW components can be utililzed besides the operation in a liquid phase also for an increase in the sensitivity during operation in the gas phase.

4. Parylene as a wave conducting layer in the gas phase.

Since the parylene coating protects the aluminum structures of the components very well from corrosion attacks and since it is extremely smooth, this coating was also tested for use in gas sensor systems. There, it is intended to serve as intermediate layer for the adaptation of the surface energies of the substrate and the sensitive polymer layer and for the production of the structures from corrosive gases.

With the deposition of a wave conducting layer on STW components (not however with RW components) in the gas sensor system a sensitivity increase should also be expected because of the initiation of Love-waves. Therefore, the dependency of the mass sensitivity of the parylene coated LW-components with increasing layer thickness was also examined in the gas phase.

For operation in the gas phase, the LW-sensors are coated with a sorption polymer, which enriches the analyte to be detected at the sensor surface. The mass change produced in the way can be detected by the change of the resonance frequency of the component. In contrast to the operation in liquids, this detection principle is reversible, the sensor does not need to be regenerated. However, care must be taken during operation of the parylene-coated LW-component that the parylene layer has little or nor sorption effects which may detrimentally affect the measuring results by delaying or increasing the signals.

Examinations performed in this connection indicate that parylene coated components exhibit only a small frequency change when exposed to organic solvent vapors. To this end, sensors with thick parylene coating (about 340 nm) were subjected to xylol since its swelling effects on parylene are known from the literature (gor 89). An application of 760 ppm xylol in $N_2$ result in a signal of less than 2 kHz.

Since for an intermediate layer, a substantially lower film thickness of between 50 and 100 $\mu$m is desired and, in the case of a 340 nm thick layer a sorption influence of maximally 1% of the total sensor signal (parylene-+sorption layer) is provided the sample application influence can be considered to be negligible.

For a stabilization of the parylene layer all the sensors were tempered in a vacuum for 3 hours at 150° C.

In the subsequent steps, all sensors were coated with a thin layer of a sorption polymer of polymethacryl acid butyl ester (PBMA). For the determination of the Love wave effect also sensor without parylene film were treated with PBMA in the same way. The sorption layer was kept as thin as possible (about 100 nm ), in order influence the propagation of the Love-waves as little as possible, but sufficiently thick to be able to measure the effects of the application of the samples.

To the sensors produced in this way alternatively samples of 3000 ppm xylol in $N_2$ was applied followed by flushing with an $N_2$ stream. By an evaluation of the frequency differences between the phase curves during exposure to the sample and during flushing at a phase position of −115° the resulting signal was obtained. FIG. 2 shows the frequency changes obtained with the exposure to the sample with 3000 ppm xylol depending on the layer thickness.

In comparison with sensors which were coated only with PBMA (see FIG. 2, 0 $\mu$m parylene), the love-wave sensor with a 0.5 $\mu$m thick parylene film and a PBMA-sorption layer provided, with the same xylol concentration, a signal which was greater by the factor 5.3.

A comparison with the measurements in liquids (135A removal) shows a similar curve with a maximum also at 0.5 $\mu$m.

Consequently, parylene can be used as a versatile coating for acoustic surface components in the gas as well as liquid sensor systems.

What is claimed is:

1. A mass-sensitive sensor consisting of an acoustic surface wave component on the basis of shear waves, said sensor having a substrate with an active surface carrying two different layers, one of said layers being an extremely smooth parylene layer of a thickness of between 0.2 and <1.6 $\mu$m as produced on said substrate by a vacuum-based deposition method and being capable of generating Love waves and the second layer forming a utilization layer, which interacts with an analyte disposed in a medium contacting said utilization layer.

2. A mass-sensitive sensor according to claim 1, wherein said utilization layer has a thickness of only a few molecules and the medium, in which the analyte is disposed, is a liquid.

3. A mass-sensitive sensor according to claim 2, wherein said parylene layer has a thickness of between 0.4 and 0.6 $\mu$m.

4. A mass-sensitive sensor according to claim 1, wherein said utilization layer comprises a sorption polymer with a thickness of between 100 and 200 nm and the medium in which the analyte is contained is a gas.

5. A mass-sensitive sensor according to claim 4, wherein said parylene layer has a thickness of between 0.4 and 0.8 $\mu$m.

6. A mass-sensitive sensor according to claim 1, wherein said acoustic surface wave component is in the form of a resonator.

7. A mass-sensitive sensor according to claim 1, wherein said acoustic surface wave component is designed for operating frequencies of between 200 and 1000 MHz.

8. A mass-sensitive sensor according to claim 1, wherein said substrate of the acoustic surface wave component consists of lithium tantalate and the operating frequency is about 380 MHz.

* * * * *